(12) United States Patent
Tominaga et al.

(10) Patent No.: US 6,228,892 B1
(45) Date of Patent: *May 8, 2001

(54) ANTIALLERGIC AGENTS

(75) Inventors: Takanari Tominaga; Eiji Nishiyama; Michio Hagiya; Nobuto Koyama; Ikunoshin Kato, all of Otsu (JP)

(73) Assignee: Takara Shuzo Co., Ltd. (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,883
(22) PCT Filed: Mar. 18, 1998
(86) PCT No.: PCT/JP98/01150
  § 371 Date: Nov. 15, 1999
  § 102(e) Date: Nov. 15, 1999
(87) PCT Pub. No.: WO99/01119
  PCT Pub. Date: Jan. 14, 1999

(30) Foreign Application Priority Data

Jul. 2, 1997 (JP) ................................................. 9-190785

(51) Int. Cl.[7] .................................................. A61K 31/12
(52) U.S. Cl. .......................... 514/690; 514/826; 514/862; 514/885; 514/886; 426/590; 426/531; 426/625; 426/653
(58) Field of Search .................................. 514/690, 885, 514/826, 862, 886; 426/590, 531, 625, 653

(56) References Cited

U.S. PATENT DOCUMENTS 5,149,711   9/1992   Hazato et al. ........................ 514/548
6,087,401   7/2000   Koyama et al. ..................... 514/690

FOREIGN PATENT DOCUMENTS

| 0974347 | 1/2000 | (EP) . |
| 0978277 | 2/2000 | (EP) . |
| 098278 | 2/2000 | (EP) . |
| 1008345 | 6/2000 | (EP) . |
| 98-13328 | 4/1998 | (WO) . |

OTHER PUBLICATIONS

Cocu et al, Helvetica Chimica Acta, vol. 55, Fasc. 8 (Apr. 1972), Nr. 286, 2838–2844, "Recherches Dans La Serie Des Cyclitols".*

Ahmad et al, Carbohydrate Research, 247 (Jun. 1993) 217–222, "On the Formation of Reductic Acid From Pentoses or Hexuronic Acids".*

Translation of Japanese Patent Publication (Kokai) No. Sho–50–70597 (1973).

Wilson et al., Ann. N.Y. Acad. Sci., vol. 804, pp. 276–83 (abstract) 1996.

* cited by examiner

Primary Examiner—Frederick Krass
(74) Attorney, Agent, or Firm—Kennedy Covington Lobdell & Hickman, L.L.P.

(57) ABSTRACT

An antiallergic agent which is characterized in containing at least one compound selected from a group consisting of 4,5-dihydroxy-2-cyclopenten-1-one represented by the following formula [I] and an optically active substance and a salt thereof as an effective component.

[I]

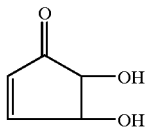

1 Claim, 3 Drawing Sheets

ANTIALLERGIC AGENTS

This application is a 371 of PCT/JP98/01150, filed Mar. 18, 1998.

TECHNICAL FIELD OF THE INVENTION

The present invention relates to drug, food and beverage which are useful for therapy of allergic diseases.

Prior Art

In allergic diseases represented by asthma and atopic dermatitis, release of chemical mediators from mast cells plays a big role in the allergic reaction. This reaction is induced by binding the immunoglobulin E (IgE) to receptors on cell membranes followed by cross-linking and it is expected that an inhibitor of the IgE production plays an effect for therapy and prevention of allergic diseases.

The reaction of the delayed type hypersensitivity is an inflammatory reaction depending upon cellular immune induced by T lymphocytes activated by antigen which is not removed by macrophage. Inflammatory cells are induced and activated by cytokine which is produced from activated T lymphocytes and release various inflammatory mediators to induce tissue disturbances. Allergic dermatitis by a reaction of the delayed type hypersensitivity occupies a high percentage of contact-type dermatitis and, in addition, it is a cause of onset of allergy where bacteria, virus or drugs are antigens. Thus, it is expected that an inhibitor of the delayed type hypersensitivity plays an effect for therapy and prevention of those allergic diseases.

Problems to be Solved by the Invention

An object of the present invention is to develop a compound which is effective for controlling the IgE production and for inhibiting the reaction of the delayed type hypersensitivity and to offer a drug which is useful for the therapy of allergic diseases containing said compound as an effective component, a method for the inhibition of allergy using said compound as an effective component and food and beverage containing said compound.

Means to Solve the Problem

In order to achieve the above-mentioned object, the present inventors have conducted an intensive investigation and found that 4,5-dihydroxy-2-cyclopenten-1-one which is a compound represented by the formula [I] (hereinafter, just referred to as "the cyclopentenone") has an inhibition activity of IgE production and an inhibition activity of delayed type hypersensitivity, and said compound is useful as an effective component of an antiallergic agent whereupon the present invention has been accomplished.

Outline of the present invention is that the first feature of the present invention relates to an antiallergic agent which is characterized in containing at least one compound selected from a group consisting of 4,5-dihydroxy-2-cyclopenten-1-one represented by the following formula [I] and an optically active substance and a salt thereof as an effective component.

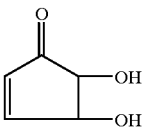

[I]

The second feature of the present invention relates to a method for inhibiting allergies which is characterized in using at least one compound selected from a group consisting of 4,5-dihydroxy-2-cyclopenten-1-one represented by the above-mentioned formula [I] and an optically active substance and a salt thereof as an effective component.

The third feature of the present invention relates to an antiallergic food or beverage which is characterized in containing at least one compound selected from a group consisting of 4,5-dihydroxy-2-cyclopenten-1-one represented by the above-mentioned formula [I] and an optically active substance and a salt thereof as an effective component.

EMBODIMENTS OF THE INVENTION

Figure 1:
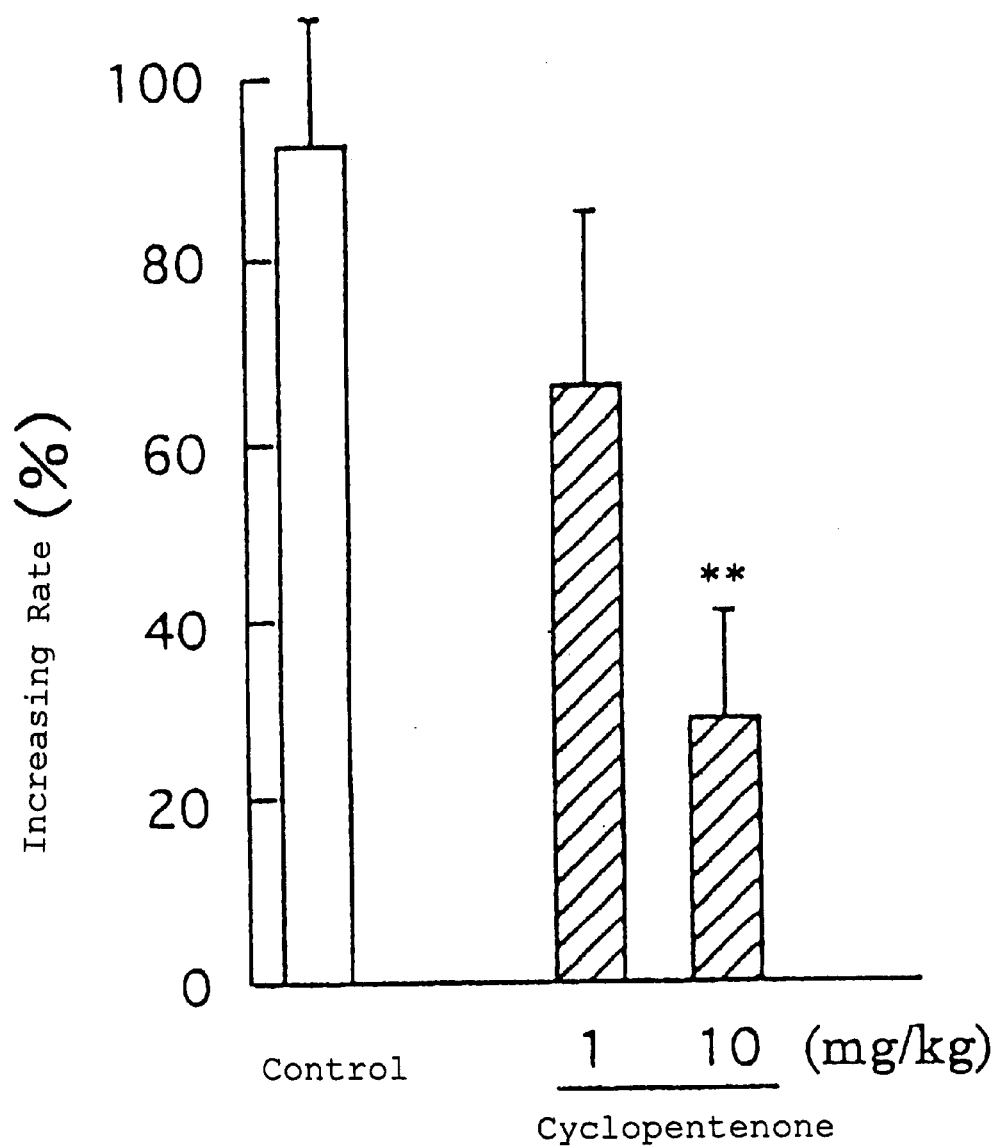
FIG. 1 shows the an inhibition activity of the cyclopentenone to reaction of the delayed type hypersensitivity.

The present invention will now be specifically illustrated as hereinafter.

The cyclopentenone represented by the formula [I] used in the present invention covers both isomers where the configurations of hydroxyl groups at 4- and 5-positions are cis- and trans. In the present invention, any of cis-cyclopentenone, trans-cyclopentenone and a mixture of cis- and trans-cyclopentenone may be used. It is also possible to use optically active substances thereof.

cis-Cyclopentenone may be prepared by a chemical synthesis [Helvetica Chimica Acta, volume 55, pages 2838–2844 (1972)]. trans-Cyclopentenone may be prepared either by a chemical synthesis [Carbohydrate Res., volume 247, pages 217–222 (1993)] or by heating uronic acid such as glucuronic acid, uronic acid derivative such as glucuronolactone or a substance containing the same (refer to PCT/JP97/03052). In the present invention, it is also possible to use such a heated product or partially purified product or purified product thereof.

For example, when D-glucuronic acid is used as a uronic acid and its 1% solution is heated at 121° C. for four hours, the cyclopentenone is produced in the heat-treated substance. The cyclopentenone in this heat-treated substance is extracted with a solvent and the extract is concentrated. Then, this concentrated extract is separated by means of a silica gel column chromatography, the eluted cyclopentenone fraction is concentrated, the cyclopentenone is extracted with chloroform from the concentrate and the extract of the concentrate is subjected to a normal phase column chromatography whereupon the cyclopentenone in the heat-treated substance is isolated.

Physical property of the cyclopentenone will be given as hereunder. Incidentally, a mass spectrometric analysis of the cyclopentenone was conducted using a mass spectrometer DX302 (manufactured by Nippon Denshi). Further, measurement of an NMR using heavy chloroform as a solvent was conducted by JNM-A 500 (manufactured by Nippon Denshi). Specific rotation was measured by a DIP-370 polarimeter (manufactured by Nippon Bunko); ultraviolet absorption spectrum was measured by a UV-2500 spectrophotometer (manufactured by Shimadzu); and infrared absorption spectrum (IR) was measured by an FTIR-8000 infrared spectrophotometer (manufactured by Shimadzu).

MS m/z 115 [M+H]$^+$;

$^1$H-NMR (CDCl$_3$): δ 4.20 (1H, d, J=2.4 Hz, 5-H), 4.83 (1H,m, 4-H), 6.30 (1H, dd, J=1.2, 6.1 Hz, 2-H), 7.48 (1H, dd, J=2.1, 6.1 Hz, 3-H).

Incidentally, the chemical shift value of the $^1$H-NMR was given on a basis that the chemical shift value of CHCl$_3$ was 7.26 ppm.

Optical rotation: $[\alpha]_D^{20}$ 0° (c 1.3, water);

UV: $\lambda_{max}$ 215 nm (water);

IR (KBr method): absorptions were noted at 3400, 1715, 1630, 1115, 1060, 1025 cm$^{-1}$.

When the isolated cyclopentenone is subjected to an optical resolution, (−)-4,5-dihydroxy-2-cyclopenten-1-one and (+)-4,5-dihydroxy-2-cyclopenten-1-one are obtained. It goes without saying that the cyclopentenone obtained by a synthetic method can be subjected to an optical resolution as well.

For example, the cyclopentenone is dissolved in ethanol. To this ethanolic solution is further added hexane/ethanol (94/6) to prepare a cyclopentenone solution. The cyclopentenone can be optically resolved when this sample solution is subjected to an HPLC using, for example, a Chiral Pack AS (manufactured by Daicel Chemical Industries) under such a condition that the column temperature was 40° C. and the mobile phase was hexane/ethanol (94/6).

Optical rotation of the optically resolved (−)-trans-4,5-dihydroxy-2-cyclopenten-1-one [hereinafter, referred to as (−)-cyclopentenone] is $[\alpha]_D^{20}$ −105° (c 0.30, ethanol) while that of the optically resolved (+)-trans-4,5-dihydroxy-2-cyclopenten-1-one [hereinafter, referred to as (+)-cyclopentenone] is $[\alpha]_D^{20}$ +104° (c 0.53, ethanol). Incidentally, the optical rotation was measured by the above-mentioned polarimeter of the type DIP-370 (manufactured by Nippon Bunko).

After that, each of (−)-cyclopentenone and (+)-cyclopentenone was subjected to structural analysis by means of mass analysis and nuclear magnetic resonance (NMR), measurement of UV absorption spectrum and measurement of infrared absorption spectrum by the method mentioned already. As a result, both optically active substances showed the same result as that of the cyclopentenone before the optical resolution.

Each of the optically resolved (−)-cyclopentenone and (+)-cyclopentenone was converted to a p-dimethylaminobenzoyl derivative, the circular dichroism spectrum (CD) was measured using a circular dichroism dispersimeter of type J-720 (manufactured by Nippon Bunko) and the result was applied to a dibenzoate chirality rule [J. Am. Chem. Soc., volume 91, pages 3989–3991 (1969)] to determine the configuration.

Figure 2:
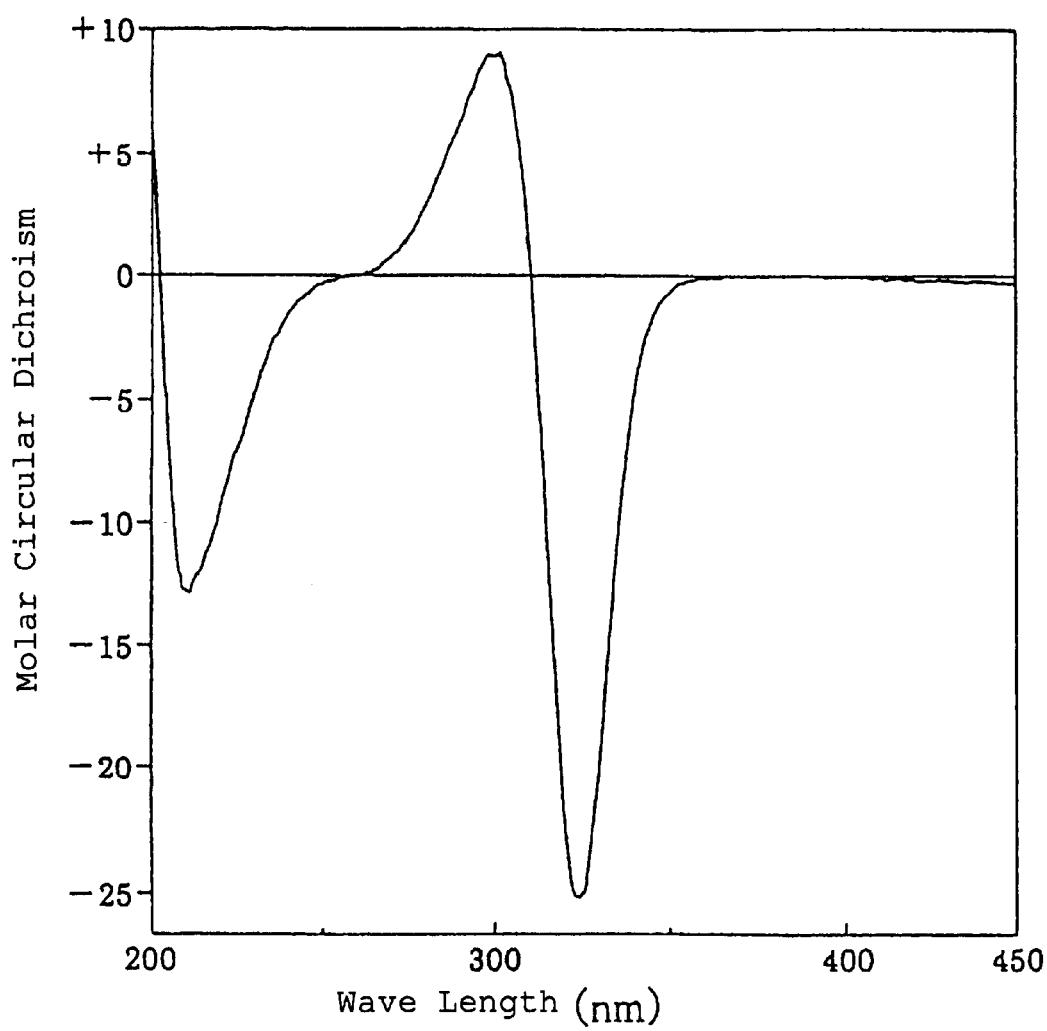
FIG. 2 shows a CD of p-dimethylaminobenzoyl derivative of (−)-cyclopentenone and a stereostructure of (−)-cyclopentenone.
Figure 2:
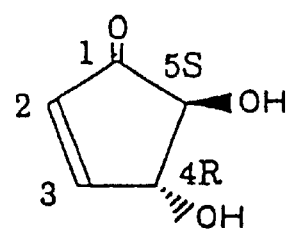

CD of p-dimethylaminobenzoyl derivative of (−)-cyclopentanone and stereostructure of (−)-cyclopentenone are shown in FIG. 2. In the drawing, the ordinate indicates molar circular dichroism while the abscissa indicates wave length (nm). Incidentally, the above stereostructure is given hereunder as the formula [II]

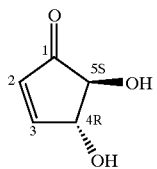

[II]

Figure 3:
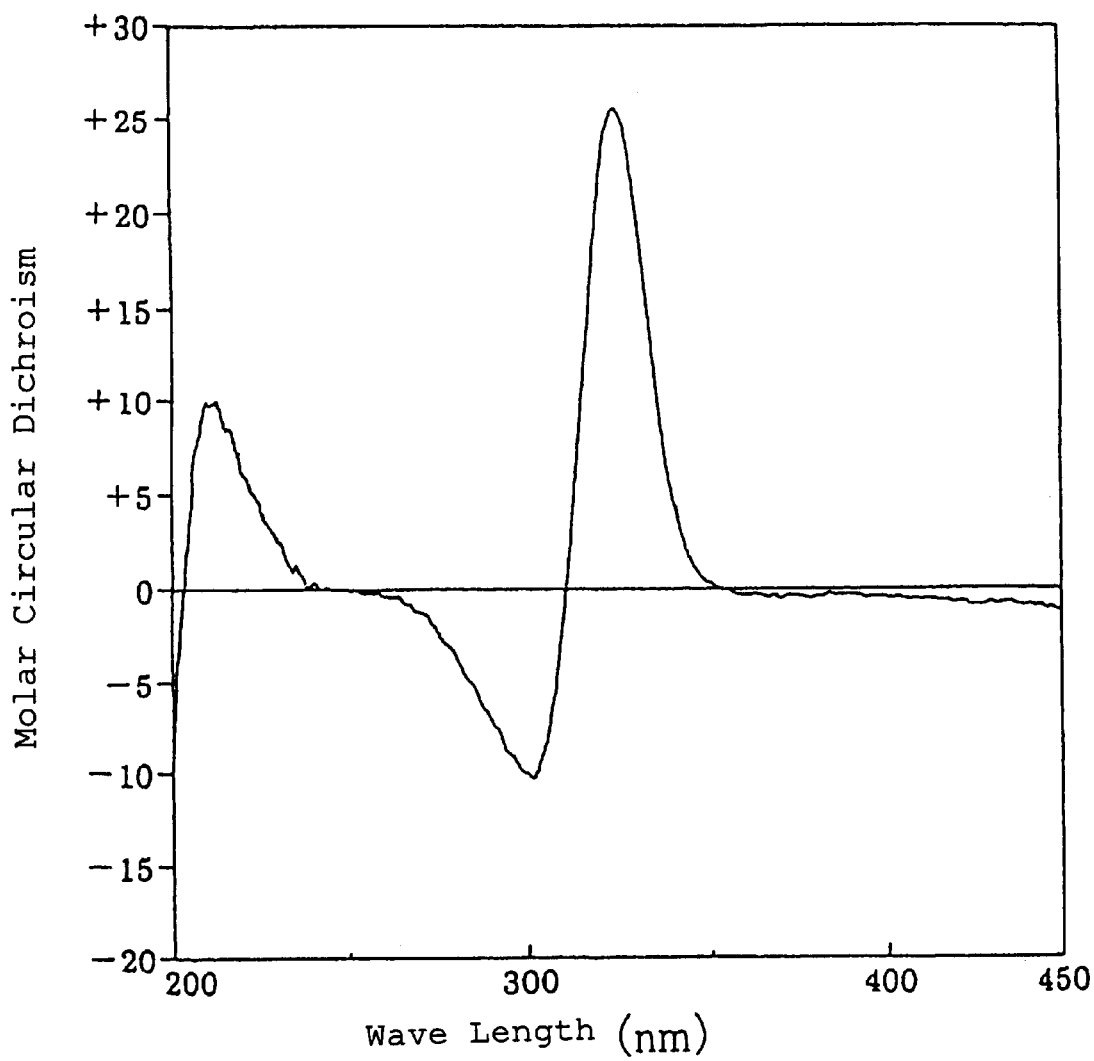
FIG. 3 shows a CD of p-dimethylaminobenzoyl derivative of (+)-cyclopentenone and a stereostructure of (+)-cyclopentenone.
Figure 3:
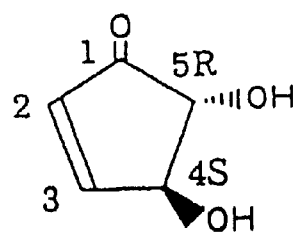

CD of p-dimethylaminobenzoyl derivative of (+)-cyclopentanone and stereostructure of (+)-cyclopentenone are shown in FIG. 3. In the drawing, the ordinate indicates molar circular dichroism while the abscissa indicates wave length (nm). Incidentally, the above stereostructure is given hereunder as the formula [III]

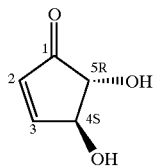

[III]

As shown in FIG. 2, FIG. 3, formula [II] and formula [III], the (−)-cyclopentenone is (−)-(4R, 5S)-trans-4,5-dihydroxy-2-cyclopenten-1-one while the (+)-cyclopentenone is (+)-(4S, 5R)-trans-4,5-dihydroxy-2-cyclopenten-1-one.

The above-mentioned cyclopentenones or an optically active substance thereof may be manufactured by any method, i.e. they may be manufactured by a method disclosed in this specification or by means of chemical synthesis; and trans- and cis-cyclopentenone or a mixture thereof and an optically active substance thereof may be used in the present invention as well.

Examples of the salt of the cyclopentenone or optically active substance thereof are pharmaceutically acceptable salts and they may be prepared by known converting methods.

The cyclopentenone reacts, for example, with an SH-containing compound (such as cysteine and glutathione) in vivo to produce a metabolic derivative which is useful as a drug. Therefore, it is believed that the pharmaceutical effect of the metabolic derivative is achieved even when the cyclopentenone is administered as well. The reaction product of the cyclopentenone with an SH-containing compound in vivo is presumed to be one of the metabolically effective substances.

Thus, when exemplification is done for an SR-containing compound (R-SH), it reacts with the SH-containing compound to give a compound represented, for example, by the following formula [IV] or [V]. In addition, a compound represented by the formula [V] is converted to a compound represented by the formula [IV].

As such, the cyclopentenone is converted to each of the metabolic derivatives in the presence of an R-SH and such a metabolic derivative produced in vivo achieves an effect as a drug too.

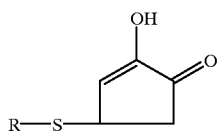

[IV]

(R is a residual group where an SH group is removed from the SH-containing compound.)

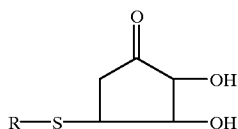

[V]

(R is a residual group where an SH group is removed from the SH-containing compound.)

Accordingly, the use of the cyclopentenone, its optically active substance or salt thereof having an object of production of such a reaction product in vivo, i.e. a metabolic derivative, is covered by the present invention as well.

When at least one compound selected from the cyclopentenone, its optically active substance or salt thereof having an inhibition activity of IgE production and an inhibition activity of delayed type hypersensitivity is used as an effective component and is made into a pharmaceutical preparation by combining with known pharmaceutical carriers, it is now possible to prepare anantiallergic agent. Generally, at least one of the compound selected from the cyclopentenone, its optically active substance or salt thereof is compounded with a pharmaceutically acceptable liquid or solid carrier and, if necssary, solvent, dispersing agent, emulsifier, buffer, stabilizer, filler, binder, disintegrating agent, lubricant, etc. are added thereto to give said pharmaceutical preparation which may be in solid such as tablets, granules, diluted powders, powders, capsules, etc. or in liquid such as solutions, suspensions, emulsions, etc. Further, this may be in a dry preparation which can be made into liquid by adding an appropriate carrier before use.

The pharmaceutical carrier may be selected depending upon the above-mentioned mode of the administration and form of the preparation. In the case of oral preparations, starch, lactose, sugar, mannitol, carboxymethyl cellulose, corn starch, inorganic salts, etc. may be used. In the manufacture of oral preparations, binders, disintegrating agents, surface-active agents, lubricants, fluidity promoters, taste-correctives, coloring agents, flavors, etc. may be further compounded therewith.

On the other hand, in the case of parenteral preparations, they may be prepared by common methods where at least one of the compound selected from the cyclopentenone, its optically active substance or salt thereof which is an effective component of the present invention is dissolved or suspended in a diluent such as distilled water for injection, physiological saline solution, aqueous solution of glucose, vegetable oil for injection, sesame oil, peanut oil, soybean oil, corn oil, propylene glycol, polyethylene glycol, etc. followed, if necessary, by adding bactericides, stabilizers, isotonic agents, analgesics, etc. thereto.

The antiallergic agent of the present invention can be administered by an appropriate route depending upon the dosage form. There will be no particular limitation for the administering route and may be conducted by oral or external means or by injection. For example, tablets, pills, granules, diluted powder, liquid, suspension, syrup and capsules may be orally administered. Injection may be administered, for example, intravenously, intramuscularly, subcutaneously or intracutaneously. Ointment, cream, etc. may be administered percutaneously. Suppositories may be administered per rectum. It is also possible to prepare aqueous or non-aqueous eye drops and examples of the eye drops to be administered to eye are ophthalmic ointment, painting liquid, sprinkling preparation and inserting preparation. For inhalation, a solution or a suspension of the effective component in common pharmaceutical vehicles is used and is applied, for example, as an aerosol spray for inhalation. It is also possible that dry and powdery effective component is administered using an inhaling device or the like so that the component can directly contact the lung.

The dose as an antiallergic agent is not particularly specified but may be appropriately determined depending upon the dosage form, administration method, purpose of the use and age, body weight, conditions, etc. of the patient. Usually, however, the amount of at least one of the compound selected from the cyclopentenone, an optically active substance thereof or a salt thereof contained in the preparation for an adult is 10pg-50 mg/kg per day. As a matter of course, the dose may vary depending upon various factors and, therefore, the dose less than the above-mentioned one may be sufficient in some cases while, in other cases, the dose more than the above may be necessary. The agent of the present invention may be administered orally as it is and, further, the agent maybe taken daily after adding to common food and/or beverage as well.

An inhibitor of the IgE production and an inhibitor of the delayed type hypersensitivity containing at least one compound selected from the cyclopentenone, an optically active substance thereof or a salt thereof as an effective component can be made into a pharmaceutical preparation by the same manner as in the case of the above-mentioned antiallergic agent and can be administered by the same manner as in the case of the antiallergic agent.

Further, the cyclopentenone, an optically active substance thereof or a salt thereof may be used as a material for the antiallergic food or beverage. When the cyclopentenone, an optically active substance thereof or a salt thereof is taken, symptoms of the diseases caused by the IgE production and delayed type hypersensitivity can be significantly improved and, in addition, said compound has an excellent preventive activity to said diseases as well.

There is no particular limitation for the method of manufacturing antiallergic food or beverage but cooking, processing and commonly-used manufacturing methods for food or beverage may be applied provided that at least one compound selected from the cyclopentenone, an optically active substance or a salt thereof having an inhibition activity of IgE production and an inhibition activity of delayed type hypersensitivity is contained in the resulting food or beverage as an effective component.

There is no particular limitation for the shape of antiallergic food or beverage so far as at least one compound selected from the cyclopentenone, an optically active substance or a salt thereof having an antiallergic action is contained therein, added thereto and/or diluted therein as an effective component. Thus, the shape includes the ones which can be orally taken such as tablets, granules, capsules, gel and sol.

A method for the inhibition of allergy offered by the use of the cyclopentenone or optically active substance or salt thereof as an effective component is useful in a study of onset mechanism of allergy and in a screening of antiallergic agents.

Therefore, the drug, food or beverage inhibits the IgE production and is very useful for improvement and/or therapy of the diseases which is mediated or worsened by the IgE production such as allergic diseases caused by the IgE including bronchial asthma, allergic rhitinis, atopic dermatitis, allergic conjunctivitis, urticaria and anaphylactic shock. It also inhibits the delayed type hypersensitivity and is useful for therapy and prevention of the diseases accompanied by a delayed type hypersensitivity such as contact sensitivity, allergic contact dermatitis, bacterial allergy, fungal allergy, viral allergy, drug allergy, thyroiditis and allergic encephalitis.

No toxicity was observed in the compound used in the present invention even when the dose which is effective to achieve those physiological activities is administered. In the case of oral administration for example, no dead case was observed in rats by a single oral administration of 100 mg/kg of any of the cyclopentenone, an optically active substance or a salt thereof.

EXAMPLES

The present invention will be further illustrated by way of the following examples although the present invention is never limited to those examples. Incidentally, "%" used in the examples stands for "% by weight".

Referential Example 1

D-Glucuroic acid (G 5269; manufactured by Sigma) (10 g) was dissolved in 1 liter of water, heated at 121° C. for four hours and concentrated in vacuo until about 10 ml. This was mixed with 40 ml of an upper layer of a 3:2:2 mixture of butyl acetate, acetic acid and water and centrifuged and the resulting supernatant liquid was concentrated in vacuo until about 10 ml.

The above extract was applied to silica gel (BW-300SP,; 2×28 cm; manufactured by Fuji Silycia) for a column chromatography and separated using an upper layer of a 3:2:2 mixture of butyl acetate, acetic acid and water as an eluate at the flow rate of about 5 ml/minute under a pressure of 0.2 kg/cm$^2$ using a compressor. Fractionation was conducted to make a volume of one fraction 10 ml and a part of each fraction was analyzed by a thin layer chromatography whereupon cyclopentenone of a high purity was contained in 61st to 80th fractions. Those fractions were collected, concentrated in vacuo, extracted with 40 ml of chloroform and the extract was concentrated in vacuo to afford 100 mg of cyclopentenone.

The fraction was separated by means of a normal phase HPLC using a Palpack type S column and, when a detection was conducted by an ultraviolet absorption of 215 nm, the purity was found to be 98%.

The above cyclopentenone (113.9 mg) was dissolved in 2.85 ml of ethanol. To this ethanolic solution was added 3.85 ml of hexane/ethanol (94/6) to prepare a cyclopentenone solution (17 mg/ml). This solution was filtered through a filter of 0.5 µm to prepare a sample solution for an optical resolution HPLC.

This sample solution was applied to an optical resolution HPLC, each of the fractions of the (−)-cyclopentenone in the earlier peak and the (+)-cyclopentenone in the later peak was collected and evaporated to dryness in vacuo to give 43.2 mg of the (−)-cyclopentenone and 43.0 mg of the (+)-cyclopentenone.

Conditions for Optical Resolution HPLC.

Columns: Chiral Pack AS (manufactured by Daicel) 2.0 cm×25.0 cm

Column temperature: 40° C.

Mobile phase: hexane/ethanol (94/6)

Flow rate: 14.0 ml/minute

Detection: UV 210 nm

Amount of the charged sample: 150 µl (2.55 mg).

Each of the (−)-cyclopentenone and (+)-cyclopentenone obtained herein contains about 1% of enantiomer and, therefore, they were subjected to an optical resolution under the above-mentioned conditions again. As a result, 19.7 mg of the (−)-cyclopentenone containing no enantiomer was obtained from 30.0 mg of the (−)-cyclopentenone of the earlier peak while, from 37.4 mg of the (+)-cyclopentenone of the later peak, 27.7 mg of the (+)-cyclopentenone containing no enantiomer was obtained. Incidentally, the eluting times in optical resolution HPLC of the (−)-cyclopentenone and (+)-cyclopentenone were 33 minutes and 40 minutes, respectively.

Example 1

(1) BALB/c male mice (Nippon Clare) (five weeks age; five mice per group) were sensitized by intraperitoneal administration of 100 µl of 0.01% physiological saline solution of egg white albumin (Sigma) and 100 µl of alum (trade name: Imject Alum; Pearce) and, 11 days thereafter, peripheral blood was collected from vein of eyeground.

The collected blood was centrifuged (2,000 rpm for five minutes), plasma was separated and the total IgE amount in the plasma was measured by means of ELISA (IgE Mouse EIA Kit; Seikagaku Corporation).

In the group to which the cyclopentenone was administered, 10 mg/kg was compulsorily administered per os once daily from the date of antigen sensitization until the day before the blood collection.

In the control group, distilled water was orally administered by the same manner as above and the non-sensitized group was named as a non-treated group.

The result is given in Table 1. An increase in total IgE. amount in plasma by sensitization with egg white albumin was suppressed by administration of the cyclopentenone.

TABLE 1

|  | Total IgE Amount in Plasma (ng/ml) Average ± SEM |
|---|---|
| Non-Treated Group | 0 |
| Control Group | 742.6 ± 366.0 |
| Cyclopentenone-Given Group | 355.8 ± 127.5 |

(2) Male rats of Wistar strain of five weeks age (one group consisting of five rats) (Nippon SLC) were sensitized by an intraperitoneal injection of 100 µl of 0.01% solution of egg white albumin (Sigma) in an aqueous physiological saline solution and 100 µl of Alum (trade name: Imject Alum; Pierce) and, after 14 days, blood was collected from abdominal artery.

The collected blood was centrifuged (at 2000 rpm for five minutes), plasma was separated and the amount of antigen-specific IgE was measured by a 48-hour rat passive cutaneous anaphylaxis (PCA) reaction.

Thus, serum was diluted with a physiological saline solution in a successively doubling manner ranging from ¼ to ¹⁄₆₄ and each 0.1 ml thereof was subcutaneously injected to hair-clipped back of male rats of Wistar strain of seven weeks age. After 48 hours from the subcutaneous injection, 1 ml of a mixture of 0.05% egg white albumin and 0.5%

Evans Blue (manufactured by Nacalai Tesque) was injected from tail vein. After 30 minutes from the injection from the tail vein, rats were subjected to decapitation and to exanguinated death, blue spots appeared on the back were observed, the spots with a diameter of 5 mm or more were judged to be positive and the highest dilution was adopted as an IgE titer.

In the cyclopentenone-administered groups, 1 mg/kg or 10 mg/kg of cyclopentenone was intraperitoneally administered once daily for three days from the antigen-sensitized day while, in the control group, distilled water was intraperitoneally administered by the same manner.

TABLE 2

| | IgE Titer |
|---|---|
| Control Group | 64 |
| Cyclopentenone-administered groups | |
| 1 mg/kg/day | 16 |
| 10 mg/kg/day | <4 |

An increase in the antigen-specific IgE amount by sensitization with egg white albumin was inhibited by administration of cyclopentenone in a dose-dependent manner.

As such, the IgE production was inhibited by the cyclopentenone. Similar inhibition activity of IgE production was noted in (−)-cyclopentenone and (+)-cyclopentenone.

Example 2

C57BL/6 mice (female, five weeks age, weighed about 20 g) were purchased from Nippon SLC and used for the experiment: after a preliminary breeding for one week at our end. Ovine erythrocyte (manufactured by Shimizu Jikken Zairyo) which is an antigen provoking the reaction of the delayed type hypersensitivity was washed three times with a physiological saline solution (manufactured by Otsuka Pharmaceutical) to make $1'10^9$ cells/ml and 200 $\mu$l of it was intraperitoneally injected to mice to subject to an antigen sensitization.

After five days from the sensitization, 40 $\mu$l of antigen which was prepared by the same manner was injected to right paw to induce an antigen whereby pedal edema was provoked. From the antigen-sensitized date, cyclopentenone was intraperitoneally administered to mice (one group consisting of five mice) once daily at the dose of 1 mg/kg or 10 mg/kg for three days.

After two days from the antigen induction, volume of right paw of the mice was measured by a measuring device for pedal edema (manufactured by Ugo Basile) and used as an index for DTH. The measured value was given by calculating the increasing rate from the right paw volume of the mice measured before the antigen induction.

The result is shown in FIG. 1. Thus, FIG. 1 shows the an inhibition activity of the cyclopentenone to reaction of the delayed type hypersensitivity where the ordinate indicates an increasing rate (%) while the abscissa indicates a dose of the cyclopentenone (mg/kg). Incidentally, ** in the drawing means that it is significant to the control in p<0.01.

Administration of 1 mg/kg of the cyclopentenone suppressed the reaction of the delayed type hypersensitivity and administration of 10 mg/kg showed a significant inhibition activity to reaction of the delayed type hypersensitivity.

Incidentally, (−)-cyclopentenone and (+)-cyclopentenone showed similar effects as well.

Example 3

Injection Preparations.

(1) Cyclopentenone was added to a physiological saline solution (as listed in the Japanese Pharmacopoeia) in a concentration of 1% to prepare an injection preparation.

(2) (−)-Cyclopentenone and glycyrrhizic acid were added to a physiological saline solution (the same as above) in concentrations of 0.5% and 0.1%, respectively, to prepare an injection preparation.

Example 4

Tablets.

(1) A tablet containing 100 mg of cyclopentenone and an appropriate amount of microcrystalline cellulose was prepared and coated with sugar to manufacture a tablet preparation.

(2) A tablet containing 0.1 mg of (+)-cyclopentenone, 10 mg of dipotassium glycyrrhizinate and an appropriate amount of microcrystalline cellulose was prepared and coated with sugar to manufacture a tablet preparation.

MERIT OF THE INVENTION

In accordance with the present invention, an antiallergic agent containing at least one compound selected from the cyclopentenone or optically active substances thereof or salts thereof having an inhibition activity of IgE production and an inhibition activity of delayed type hypersensitivity as an effective component is offered.

Because of the inhibition activity of IgE production and the inhibition activity of delayed type hypersensitivity of the cyclopentenone or optically active substance or salt thereof, when food or beverage containing such a compound is taken, the IgE production is inhibited and reaction of the delayed type hypersensitivity is inhibited whereupon such a food or beverage is an antiallergic food or antiallergic beverage which is quite useful for improvement of symptoms of the diseases mediated by the IgE production and worsened by production of said factor such as bronchial asthma, allergic rhinitis, atopic dermatitis, allergic conjunctivitis, urticaria, anaphylactic shock, contact hypersensitivity, etc. and for prevention of said diseases as well. It is also useful for the therapy and prevention of the diseases accompanied by the delayed type hypersensitivity such as contact hypersensitivity, allergic contact dermatitis, bacterial allergy, fungal allergy, viral allergy, drug allergy, thyroiditis, allergic encephalitis, etc.

Furthermore, the method of the present invention is highly useful for the inhibition of allergy such as controlling the amount of IgE production.

What is claimed is:

1. A method for the inhibition of allergy, comprising administering to an individual in need of such inhibition at least one compound selected from the group consisting of 4,5-dihydroxy-2-cyclopenten-1-one represented by the following formula [I] (I)

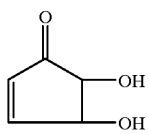

an optically active substance and a salt thereof as an effective component.

* * * * *